United States Patent [19]

Breitenstein et al.

[11] Patent Number: 4,480,106

[45] Date of Patent: Oct. 30, 1984

[54] PROCESS FOR THE PREPARATION OF ASYMMETRICALLY SUBSTITUTED MALEIC ANHYDRIDES, AND ASYMMETRICALLY SUBSTITUTED MALEIC ANHYDRIDES

[75] Inventors: Werner Breitenstein; Marcus Baumann; Hans Bosshard, all of Basel, Switzerland

[73] Assignee: Ciba-Geigy Corporation, Ardsley, N.Y.

[21] Appl. No.: 435,593

[22] Filed: Oct. 21, 1982

[30] Foreign Application Priority Data

Oct. 28, 1981 [CH] Switzerland ............... 6880/81

[51] Int. Cl.$^3$ .......................................... C07D 307/60
[52] U.S. Cl. ................................. 549/253; 546/121; 546/281
[58] Field of Search ........................ 549/253

[56] References Cited

U.S. PATENT DOCUMENTS 3,833,619  9/1974  Baumann et al. ............... 549/261
4,079,041  3/1978  Baumann et al. ............... 526/50

FOREIGN PATENT DOCUMENTS 2352216  4/1975  Fed. Rep. of Germany.

OTHER PUBLICATIONS

Reindel, Ber. Deutsch. Chem. Ges., vol. 57, pp. 1381–1386, (1924).
Tschitschibabin, Ber. Deutsch. Chem. Ber., vol. 57, pp. 2092–2101, (1924).
Clemo et al., J. Chem. Soc., pp. 2621–2628, (1928).
Muir et al., Biochem. J., vol. 45, pp. 163–170, (1949).
Plieninger et al., Annalen der Chemie, vol. 180, pp. 60–69, (1964).

Primary Examiner—Henry R. Jiles
Assistant Examiner—Bernard I. Dentz
Attorney, Agent, or Firm—Michael W. Glynn

[57] ABSTRACT

Compounds of the formula I $$R_2-CH(R_1)-CH(R)-C(=C(CH_3)-CO-O-CO-)$$ (I)

in which R, $R_1$ and $R_2$ are as defined in patent claim 1, can be prepared by a novel process, for example by treating a salt of imidazo[1,2-a]pyridin-2(3H)-one with fumaric acid, maleic acid or maleic anhydride, in the presence of a base, and converting the product to a salt of 3-(1,2-dicarboxyethyl)-imidazo[1,2-a]pyridin-2(3H)-one, in the presence of a strong acid, reacting the latter salt with a compound $CH_2=C(R_1)(R_2)$ and treating the intermediate obtained with glacial acetic acid and sodium acetate. The compounds (I) can be converted, in a manner known per se, to corresponding imides having functional groups suitable for polymerization reactions of polycondensation reactions. These imides can be used to prepare photocrosslinkable polymers. The anhydrides (I) can also be used, in some cases, to prepare pharmaceutically active benzofuranones and homosalicylic acids by reaction with salts of suitable amines.

18 Claims, No Drawings

PROCESS FOR THE PREPARATION OF ASYMMETRICALLY SUBSTITUTED MALEIC ANHYDRIDES, AND ASYMMETRICALLY SUBSTITUTED MALEIC ANHYDRIDES

The invention relates to a process for the preparation of asymmetrically substituted maleic anhydrides, to the novel asymmetrically substituted maleic anhydrides obtainable by this process, and to the novel intermediates developed for the preparation of the asymmetrically substituted maleic anhydrides. 3-Methyl-4-(2-carboxyethyl)-maleic anhydride (hematinic anhydride) can be obtained by reacting ethyl α-acetylglutarate or ethyl γ-oxo-δ-ethoxycarbonyl-caproate with HCN, if appropriate with the addition of catalytic amounts of KCN, to give the corresponding cyanohydrins, and firstly hydrolysing the cyanohydrins with concentrated HCl at temperatures of between 90° and 100° C., and then heating the products to temperatures of between 175° and 185° C. [cf., for example, J.Chem.Soc., 2,621 (1928); Biochem.J., 45, 163 (1949) and Annalen der Chemie, 680, 60 (1964)]. Because of the drastic reaction conditions required by this process, it is only suitable for the preparation of maleic anhydrides having substituents in the 3-position or 4-position which are resistant to hydrolysis. Moreover, the preparation of the starting materials required for this process is relatively complicated. On the other hand, it is known that dimethyl-maleic anhydride can be prepared by reacting particular heterocyclic, unsubstituted or N-substituted amidines or amidine salts with fumaric or maleic acid or with maleic anhydride, respectively, and subjecting the reaction products to acid hydrolysis under reflux conditions [cf., for example, German Offenlegungsschriften No. 2,233,889 and 2,233,862].

A novel, broadly applicable and simple process for the preparation of asymmetrically substituted maleic anhydrides has now been found, by which it is also possible to prepare maleic anhydrides having substituents in the 3-position or 4-position which are sensitive to hydrolysis, for example substituents containing nitrile or ester groups.

The invention thus relates to a novel process for the preparation of compounds of the formula I

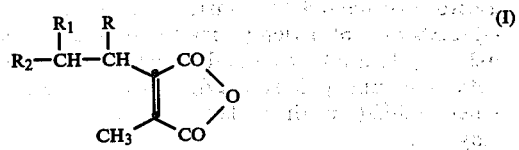

in which R is hydrogen, $C_{1-7}$-alkyl or phenyl which is unsubstituted or substituted by halogen, methoxy or $C_{1-4}$-alkyl, $R_1$ is hydrogen, $C_{1-7}$-alkyl, cyclopentyl, cyclohexyl or phenyl which is unsubstituted or substituted by halogen, methoxy or $C_{1-4}$-alkyl, or R and $R_1$ together are $-(CH_2)_3-$ or $-(CH_2)_4-$, and $R_2$ is $-CO-C_{1-8}$-alkyl, $-CO-$phenyl which can be substituted by $C_{1-4}$-alkyl, $-CN$, $-COO-C_{1-4}$-alkyl, $-COO-$allyl or $-COOH$, or in which $R_1$ is hydrogen and R and $R_2$ together are $-(CH_2)_3-CO-$, the carbonyl group in the ring formed in this way being in the m-position relative to the $-CH-$ group which is attached to R, which process comprises (a) in the case where R=H, firstly treating a compound of the formula II

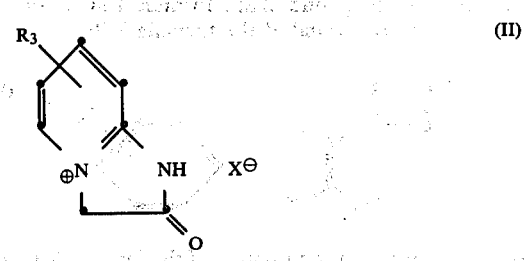

with fumaric acid, maleic acid or maleic anhydride, in the presence of a base, and then converting the product to a compound of the formula III

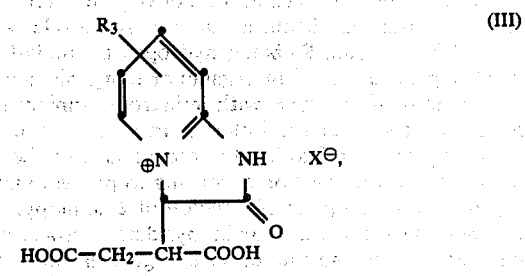

in the presence of a strong acid, reacting the compound of the formula III with a compound of the formula IVa $$CH_2=C(R_1)(R_2) \qquad (IVa)$$

to give a compound of the formula V

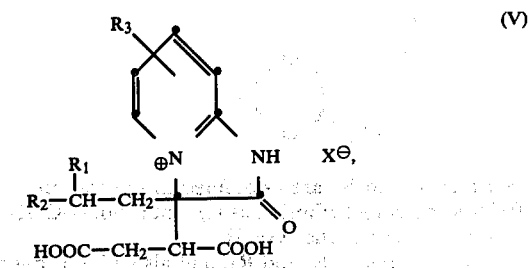

converting the compound of the formula V to a mixture of a compound of the formula I in which R=H and a compound of the formula VIa

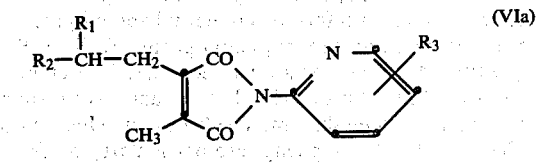

by heating to temperatures of between 80° and 160° C., and hydrolysing the compound of the formula VIa with aqueous acid to give a compound of the formula I in which R=H, or (b) in the case where R is not H, firstly treating a compound of the formula II with a compound of the formula IVb $$R'-CH=C(R_1)(R_2) \qquad (IVb),$$

in the presence of a base, and then reacting the product with fumaric acid, maleic acid or maleic anhydride, at temperatures of between 80° and 160° C., to give a mixture of a compound of the formula I in which R is not H and a compound of the formula VIb

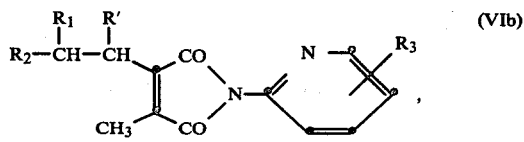

and hydrolysing the compound of the formula VIb with aqueous acid to give a compound of the formula I in which R is not H. In this process, R, $R_1$ and $R_2$ are as defined in the formula I, R' has the same definition as R, but is not H, or, together with $R_2$, is —$(CH_2)_3$—CO—, in the case where $R_1$=H, the carbonyl group in the ring formed in this way being in the m-position relative to the —CH— group, $R_3$ being hydrogen or methyl and $X^\ominus$ being the anion of an organic or inorganic acid.

Reactions of this type with imidazopyridinium salts have not been disclosed hitherto. In particular, it was surprising that, on heating the compounds of the formula V or of the reaction according to process variant (b), partial to complete elimination of 2-aminopyridine or methyl-substituted 2-aminopyridine, respectively, decarboxylation and ring closure to give the anhydride occur more or less simultaneously. The combination of these three reactions in one reaction step is unexpected and unusual.

The compounds of the formula I are novel, with the exception of hematinic anhydride (R and $R_1$=H and $R_2$=—COOH). The invention also relates to the novel compounds of the formula I'

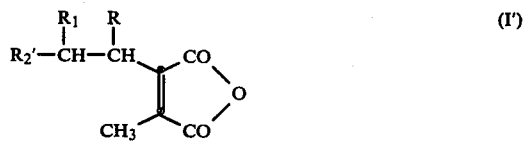

in which R and $R_1$ are as defined in the formula I and $R_2'$ has the same definition as $R_2$, but is not —COOH in the case where R and $R_1$=H.

Alkyl groups R, R' and $R_1$, and also alkyl groups, of the type defined, in radicals R, $R_1$ and $R_2$ or $R_2'$, can be straight-chain or branched. Examples of such groups are: the methyl, ethyl, n-propyl, isopropyl, n-butyl, sec.-butyl and tert.-butyl, n-pentyl, 2-pentyl, n-hexyl and n-heptyl groups. Alkyl groups having 1–4 C atoms are particularly preferred and methyl and ethyl are very particularly preferred. If phenyl groups R, R' or $R_1$ are substituted by halogen atoms, these are, for example, F, Cl or Br. Phenyl groups R, R' or $R_1$ and —CO—phenyl groups are preferably monosubstituted. Unsubstituted phenyl and —CO—phenyl are particularly preferred.

$R_3$ is preferably hydrogen.

As the anion of an organic acid, $X^\ominus$ is, for example, the anion of trifluoroacetic, benzenesulfonic, p-toluenesulfonic or methanesulfonic acid. Examples of suitable anions of inorganic acids are the anions of hydrohalic acids or of nitric, phosphoric, sulfuric or fluorosulfonic acid. $X^\ominus$ is preferably the anion of nitric or sulfuric acid or of a hydrohalic acid, especially HCl or HBr.

Preferred compounds of the formula I are those in which $R_1$ is hydrogen and R and $R_2$, or R and $R_2'$, together are —$(CH_2)_3$—CO—, or those in which R is hydrogen, $C_{1-7}$-alkyl or phenyl and $R_1$ is hydrogen, $C_{1-7}$-alkyl, cyclopentyl, cyclohexyl or phenyl, at least one of R and $R_1$ preferably being hydrogen, or R and $R_1$ together are —$(CH_2)_3$— or —$(CH_2)_4$—, and $R_2$ or $R_2'$ is —CO—$C_{1-8}$-alkyl, —CO—phenyl, —CN, —COOCH$_3$, —COOC$_2$H$_5$ or, if one of R and $R_1$ is not hydrogen, —COOH, in particular those of the formula I in which R and $R_1$ are as defined above and $R_2$ or $R_2'$ is —CO—$C_{1-8}$-alkyl or —CO—phenyl which can be substituted by $C_{1-4}$-alkyl.

Particularly preferred compounds are those of the formula I in which R and $R_1$ independently of one another are hydrogen or $C_{1-7}$-alkyl, especially $C_{1-4}$-alkyl and in particular methyl, or together are —$(CH_2)_3$— or —$(CH_2)_4$—, and $R_2$ or $R_2'$ is —CO—$C_{1-8}$-alkyl, especially —CO—$C_{1-5}$-alkyl. Very particularly preferred compounds are those of the formula I in which one of R and $R_1$ is hydrogen and the other is hydrogen or $C_{1-4}$-alkyl, in particular methyl, and $R_2$ or $R_2'$ is —CO—$C_{1-5}$-alkyl, especially —COCH$_3$ or —COC$_2$H$_5$. The most preferred compounds are those of the formula I in which R is hydrogen, $R_1$ is $C_{1-4}$-alkyl, especially methyl, and $R_2$ or $R_2'$ is —COCH$_3$.

Specific examples of novel compounds of the formula I are: 4-methyl-3-(3-oxobutyl)-maleic anhydride, 4-methyl-3-(3-oxopentyl)-maleic anhydride, 4-methyl-3-(3-oxohexyl)maleic anhydride, 4-methyl-3-(3-phenyl-3-oxopropyl)-maleic anhydride, 4-methyl-3-[3-(3- or 4-methylphenyl)-3-oxopropyl]-maleic anhydride, 4-methyl-3-[3-(4-ethylphenyl)-3-oxopropyl]-maleic anhydride, 4-methyl-3-(2-methyl-3-oxobutyl)-maleic anhydride, 4-methyl-3-(2-ethyl-3-oxobutyl)-maleic anhydride, 4-methyl-3-(2-methyl-3-oxopentyl)-maleic anhydride, 4-methyl-3-(2-cyano-1-methylethyl)-maleic anhydride, 4-methyl-3-(2-cyanoethyl)-maleic anhydride, 4-methyl-3-(2-cyano-1-phenylethyl)-maleic anhydride, 4-methyl-3-(1-methyl-3-oxobutyl)-maleic anhydride, 4-methyl-3-(1-ethyl-3-oxobutyl)-maleic anhydride, 4-methyl-3-(1-phenyl-3-oxobutyl)-maleic anhydride, 4-methyl-3-[1-(4-chlorophenyl)-3-oxobutyl]-maleic anhydride, 4-methyl-3-[1-(3- or 4-methylphenyl)-3-oxobutyl]-maleic anhydride, 4-methyl-3-[1-(4-methoxyphenyl)-3-oxobutyl]-maleic anhydride, 4-methyl-3-(3-oxocyclohexyl)-maleic anhydride, 4-methyl-3-(1,3-diphenyl-3-oxopropyl)-maleic anhydride, 4-methyl-3-(2-methoxycarbonyl-1-methylethyl)-maleic anhydride, 4-methyl-3-(2-ethoxycarbonylethyl)-maleic anhydride, 4-methyl-3-(2-n-propoxycarbonylethyl)-maleic anhydride, 4-methyl-3-(2-carboxy-1-methylethyl)-maleic anhydride, 4-methyl-3-(2-carboxy-1-phenylethyl)-maleic anhydride, 4-methyl-3-(2-cyclohexyl-3-oxobutyl)-maleic anhydride, 4-methyl-3-(2-phenyl-3-oxobutyl)-maleic anhydride and 4-methyl-3-[2-(4-methoxyphenyl)-3-oxobutyl]-maleic anhydride.

In process variant (a), it is advantageous to use maleic acid, whereas for process variant (b), maleic anhydride is preferred.

Bases which can be used for the reaction of the compounds of the formula II with fumaric acid, maleic acid or maleic anhydride, or with the compounds of the formula IVb, are organic or inorganic compounds, such as tertiary amines, in particular trialkylamines or cyclic amines, for example triethylamine, tri-n-butylamine, pyridine, picoline, quinoline and lutidine, alkali metal or alkaline earth metal hydroxides, carbonates or hydrogencarbonates, or salts of alkali metals or alkaline earth metals with weak acids, such as carboxylates, in particular acetates. It is preferred to use an alkali metal hydroxide, in particular NaOH or KOH.

The said reactions, and also the further reaction with compounds of the formula IVa according to process variant (a), can be carried out in an aqueous, aqueous-organic or organic medium. Suitable organic solvents are, in particular, polar solvents, such as alkanols having up to 6 C atoms, ethylene glycol monoalkyl ethers having up to 4 C atoms in the alkyl moiety, N,N-dialkylamides of aliphatic monocarboxylic acids having 1–3 C atoms in the acid moiety, or cyclic amides, for example methanol, ethanol, n-propanol, isopropanol, butanols and hexanols, ethylene glycol monomethyl ether and monoethyl ether, N,N-dimethylformamide, N,N-dimethylacetamide, N,N-dimethylpropionamide and N-methylpyrrolidone.

The reaction of the compounds of the formula II with fumaric acid, maleic acid or maleic anhydride is preferably carried out in an aqueous medium. For the reactions with compounds of the formula IVa or IVb, an aqueous-organic medium, especially an aqueous-alcoholic medium, is preferred. Mixtures of water and methanol are particularly preferred for these reactions.

The reaction temperatures for the reaction of the compounds of the formula II with fumaric acid, maleic acid or maleic anhydride, or with the compounds of the formula IVb, are advantageously between 0° and 80° C., especially between 20° and 50° C. For the reaction of the compounds of the formula III with the compounds of the formula IVa, reaction temperatures of between 0° and 50° C., especially of between 20° and 40° C., are preferred.

Strong acids which can be used in process variant (a) are either organic or inorganic compounds, for example trifluoroacetic acid, benzenesulfonic acid, p-toluenesulfonic acid, methanesulfonic acid, hydrohalic acids or nitric, phosphoric, sulfuric or fluorosulfonic acid. Nitric acid, sulfuric acid and hydrohalic acids, especially HCl or HBr, are preferred.

The heating of the compounds of the formula V and of the reaction mixture according to process variant (b), obtained after the addition of fumaric acid, maleic acid or maleic anhydride, can be carried out with or without the addition of a high-boiling organic solvent and, if appropriate, in the presence of a buffer, such as sodium acetate, potassium propionate, sodium hydrogenphosphate or sodium citrate. Examples of suitable solvents are unsubstituted or chlorine-substituted aromatic hydrocarbons, such as toluene, xylenes and chlorobenzene, N,N-dimethylformamide, N,N-dimethylacetamide, 1,2-diethoxyethane, propionic acid and glacial acetic acid. Preferably, the conversion to compounds of the formula I and compounds of the formula VIa or VIb is carried out at temperatures of between 90° and 110° C. and in the presence of a high-boiling organic solvent, in particular in glacial acetic acid.

For the hydrolysis of the compounds of the formula VIa or VIb, it is possible to use aqueous organic or aqueous inorganic acids, if appropriate mixed with diluents. The reaction temperatures are advantageously between 20° C. and the boiling point of the reaction medium. Suitable diluents are, in particular, water-miscible organic solvents, for example open-chain or cyclic ethers, such as 1,2-dimethoxyethane, tetrahydrofuran, tetrahydropyran and dioxane. The preferred diluent is tetrahydrofuran. Examples of suitable organic acids are trichloroacetic acid, trifluoroacetic acid, methanesulfonic acid and p-toluenesulfonic acid, and examples of suitable inorganic acids are sulfuric acid, phosphoric acid, nitric acid, hydrochloric acid and perchloric acid.

Preferably, the hydrolysis is carried out in an aqueous-inorganic acid, in particular aqueous sulfuric acid, mixed with a water-miscible organic solvent, especially tetrahydrofuran. If $R_2$ is —COO—$C_{1-4}$-alkyl or —COO-allyl in the formulae VIa and VIb, this ester group is also hydrolysed. The 2-aminopyridine or methyl-substituted 2-aminopyridine detached during the hydrolysis can be recovered virtually quantitatively and used again for the preparation of the starting compounds of the formula II.

The starting materials of the formulae II, IVa and IVb are known and can be prepared by methods known per se. Compounds of the formula II can be obtained, for example, by the process described in Ber., 57, 1,381 and 2,092 (1924).

In the process according to the invention, compounds of the formula VII

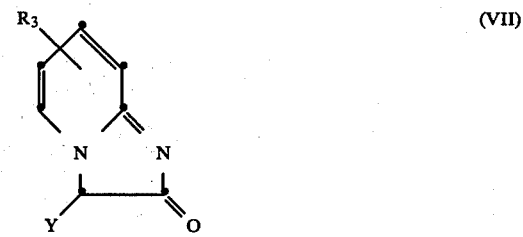

(VII)

in which $R_3$ is as defined in the formula II and Y is

HOOC—CH₂CH—COOH or —CH(R)—CH($R_1$)($R_2$), are formed as intermediates. The compounds of the formula VII, the intermediates of the formulae III and V and the free bases which can be prepared therefrom by customary methods, and also the intermediates of the formulae VIa and VIb, which were developed especially for the preparation of the compounds according to the invention, are novel and also form a subject of the invention. As regards preferred definitions, R, $R_1$, $R_2$, $R_3$ and $X^\ominus$ are as defined above. If desired, the said intermediates can be isolated in a manner known per se, for example by crystallisation. In general, however, this isolation is dispensed with. If desired, mixtures of compounds of the formulae I and VIa or VIb can also be separated in a customary manner, for example by distillation or chromatography on silica gel.

The anhydrides of the formula I can be converted, in a manner known per se, to corresponding imides, inter alia to imides having functional groups suitable for polymerisation reactions or polycondensation reactions, of the type described in German Offenlegungsschrift No. 2,626,795. From such imides having functional groups, it is possible, again in a manner known per se, to prepare photocrosslinkable polymers [cf., for example, German Offenlegungsschrift No. 2,626,795] which can be used, for example, for the production of highly photosensitive image materials, for the production of printing plates for the offset printing process, for the production of photo-offset lacquers, for unconventional photography, and, in particular, as photoresists for the production of printed circuits.

Moreover, compounds of the formula I in which R and $R_1$ independently of one another are hydrogen or $C_{1-7}$-alkyl or together are —(CH₂)₃ or —(CH₂)₄— and $R_2$ is —CO—CH$_3$ are valuable starting materials for the preparation of benzofuranones and homosalicylic acids or homosalicylic acid derivatives, salts and isomers thereof, substituted by a cyclic or N,N-disubstituted amino group, which are applied as active ingredients for medicaments. These benzofuranones and homosalicylic acids can be obtained by reacting the said compounds of the formula I with salts of suitable amines. Benzofuranones or mixtures of benzofuranones and homosalicylic acids are formed in this reaction. Homosalicylic acids can also be prepared by the hydrolysis of benzofuranones. Some typical representatives are illustrated in the examples. These benzofuranones and homosalicylic acids possess, in particular, a pronounced anti-inflammatory action, which can be demonstrated, for example, by the reduction in the oedema of the paw caused by carrageenin in rats, from a dose of about 0.1 mg/kg, administered orally, analogously to the method described by Pasquale et al., Agents and Actions 5, 256 (1976), and also in the adjuvant-arthritis model on rats, from a dose of about 10 mg/kg, administered orally, analogously to the method described by L. Riesterer and R. Jacques, Pharmacology 2, 288 (1969). Moreover, from a concentration of about 10 μmols/l, the said compounds inhibit prostaglandin synthesis from arachidonic acid, in vitro, analogously to the method described by H. L. White and A. T. Glassman, Prostaglandin 7, 123 (1974).

Furthermore, the said benzofuranones and homosalicylic acids have an antinociceptive component in their action, which can be deduced, for example, from the reduction in the writhing syndrome induced by phenyl-p-benzoquinone in mice, from a dose of about 0.1 mg/kg, administered orally [method: analogous to that described by L. C. Hendershot and J. Forsaith, J. Pharmacol. exp. Therap. 125, 237 (1959)]. They also have the ability to absorb, from the UV spectral region, those rays which produce erythema on the epidermis (between 290 and 320 nm), whilst the substances transmit the rays from about 320 to 400 nm, which have a tanning action. Consequently, these benzofuranones and homosalicylic acids can be used as antiinflammatory agents, (peripheral) analgesics and/or light stabilisers, for example for cosmetic purposes.

Pharmaceutical preparations which contain the said benzofuranones or homosalicylic acids, or salts thereof, are suitable in particular for topical application and also for enteral administration, such as oral or rectal administration, and parenteral administration to warm-blooded animals, the pharmacological active ingredient being present by itself or together with a pharmaceutically applicable carrier. The daily dosage of the active ingredient depends on the species of warm-blooded animal, the age and the individual condition, and also on the method of administration. In the normal case, for a warm-blooded animal weighing about 75 kg, an approximate daily dose would be from about 100 to about 600 mg, administered orally, advantageously divided up into several equal daily doses. Such pharmaceutical preparations contain, for example, from about 10% to about 80%, preferably from about 20% to about 60%, of the active ingredient. Examples of pharmaceutical preparations for enteral or parenteral administration are those in the form of dose units, such as sugar-coated tablets, tablets, capsules or suppositories, and also ampoules. These are prepared in a manner known per se, for example by means of conventional mixing, granulation, coating, solution or lyophilisation processes, using customary carriers and/or adjuncts. Thus, pharmaceutical preparations for oral administration can be obtained by combining the active ingredient with solid carriers, converting the mixture obtained to granules if appropriate, and processing the mixture or granules to form tablets or sugar-coated tablet cores, after the addition of suitable adjuncts if desired or necessary. Possible pharmaceutical preparations for topical application are, in particular, creams, ointments, pastes, foams, tinctures and solutions, which contain about 0.1 to about 5% of the active ingredient.

EXAMPLE 1

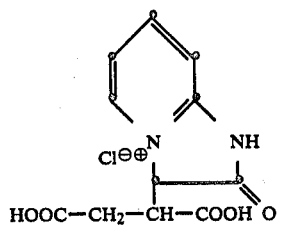

A mixture of 341 g (2 mols) of imidazo[1,2-a]pyridin-2(3H)-one hydrochloride and 700 ml of water is treated with portions of a solution of 80 g (2 mols) of sodium hydroxide in 200 ml of water, with stirring. A solution of 250.7 g (2.16 mols) of maleic acid in 600 ml of water is then added dropwise in such a way that the internal temperature of the reaction mixture remains between 40° C. and 45° C. After 30 hours at room temperature (20°–25° C.), the mixture is cooled to 5° C., the precipitate formed is filtered off, the filtrate is concentrated to about half its volume in vacuo, and the product which has precipitated is filtered off with suction. The combined residues are washed with a small amount of cold methanol and dried at 50° C. in vacuo. This gives 400 g of 3-(1,2-dicarboxyethyl)-imidazo[1,2-a]pyridin-2(3H)-one with a melting point of 193° (decomposition). The product obtained is stirred with 650 ml of concentrated hydrochloric acid at room temperature for 6 hours. After cooling to 5° C., the precipitate is filtered off, the filtrate is concentrated to about half its volume in vacuo, and the product which has precipitated is filtered off with suction. The combined residues are washed with acetone and dried at 50° C. in vacuo. This gives 350 g (61% of theory) of 3-(1,2-dicarboxyethyl)-imidazo[1,2-a]pyridin-2(3H)-one hydrochloride with a melting point of 205° C. (decomposition). IR spectrum (KBr, cm$^{-1}$): inter alia 2,970, 1,780, 1,735, 1,660, 1,535, 1,170, 1,125, 1,080, 930, 770.

EXAMPLE 2

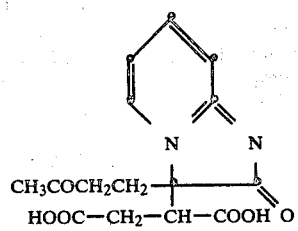

A mixture of 18.9 g (0.066 mol) of 3-(1,2-dicarboxyethyl)-imidazo[1,2-a]pyridin-2(3H)-one hydrochloride, 7 g (0.1 mol) of methyl vinyl ketone, 50 ml of methanol and 50 ml of water is stirred for 36 hours at room temperature. The product is then precipitated by the dropwise addition of about 15 ml of 4N aqueous sodium hydroxide solution. The precipitate is filtered off with suction, washed with water, methanol and acetone and dried in vacuo at 50° C. This gives 8 g (38% of theory) of 3-(1,2-dicarboxyethyl)-3-(3-oxobutyl)-imidazo[1,2-a]pyridin-2(3H)-one with a melting point of 195° C. (decomposition). $^1$H-NMR spectrum (100 MHz, d$_6$-DMSO, δ in ppm): 1.80-2.60 (m,9H); 3.34 (m,1H); 6.90 (m,1H); 7.14 (m,1H); 7.86 (m,1H); 8.16 (m,1H). IR spectrum (KBr, cm$^{-1}$): inter alia 1,770, 1,745, 1,670, 1,535, 1,240, 1,180.

EXAMPLE 3

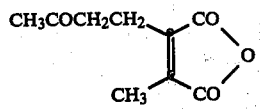

A mixture of 114.7 g (0.4 mol) of 3-(1,2-dicarboxyethyl)-imidazo[1,2-a]pyridin-2(3H)-one hydrochloride, 36.4 g (0.52 mol) of methyl vinyl ketone, 150 ml of methanol and 150 ml of water is stirred for 36 hours at room temperature and then evaporated to dryness at about 45° C. in vacuo. The crude product obtained is taken up in 300 ml of glacial acetic acid and treated with 15 g of sodium acetate, and the mixture is boiled under reflux until the evolution of CO$_2$ has ended. The solvent is then removed in vacuo, the residue is treated with a mixture of 150 ml of 6M sulfuric acid and 150 ml of tetrahydrofuran, and the resulting mixture is kept at 60° C. for 8 hours. After removal of the tetrahydrofuran in vacuo, the reaction mixture is diluted with water and extracted with methylene chloride, and the extract is filtered on silica gel. Distillation of the crude product under a high vacuum (115° C.-125° C./8 Pa) gives 34 g (47% of theory) of 4-methyl-3-(3-oxo-butyl)-maleic anhydride as a spectroscopically pure, pale yellow oil. For elementary analysis, a sample is chromatographed on silica gel with petroleum ether/diethyl ether. $^1$H-NMR spectrum (100 MHz, CDCl$_3$, δ in ppm): 2.16 (s,3H); 2.19 (s,3H); 2.60-3.00 (m,4H). IR spectrum (CH$_2$Cl$_2$, cm$^{-1}$): inter alia 1,770, 1,725, 1,170, 1,125, 925.

Elementary analysis for C$_9$H$_{10}$O$_4$ (182.2): Calculated: C 59.3%, H 5.5%; Found: C 59.4%, H 5.6%.

EXAMPLE 4

4-Methyl-3-(3-oxopentyl)-maleic anhydride is prepared in a manner analogous to that described in Example 3, using ethyl vinyl ketone in place of methyl vinyl ketone. This gives a pale yellow oil. $^1$H-NMR spectrum (100 MHz, CDCl$_3$, δ in ppm): 1.06 (t, J=7 Hz, 3H); 2.13 (s,3H); 2.44 (q, J=7 Hz, 2H); 2.58-2.92 (m,4H). IR spectrum (CH$_2$Cl$_2$, cm$^{-1}$): inter alia 1,780, 1,735, 1,120, 935.

Elementary analysis for C$_{10}$H$_{12}$O$_4$ (196.2): Calculated: C 61.2%, H 6.2% Found: C 61.1%, H 6.4%.

EXAMPLE 5

4-Methyl-3-(3-phenyl-3-oxopropyl)-maleic anhydride is prepared in a manner analogous to that described in Example 3, using phenyl vinyl ketone in place of methyl vinyl ketone; melting point: 105° C.-107° C. $^1$H-NMR spectrum (100 MHz, CDCl$_3$, δ in ppm): 2.22 (s,3H); 2.80-3.00 (m,2H); 3.32-3.50 (m,2H); 7.38-7.70 (m,3H); 7.90-8.03 (m,2H). IR spectrum (KBr, cm$^{-1}$): inter alia 1,790, 1,710, 1,280, 1,220, 1,135, 980, 930, 895, 750, 735.

Elementary analysis for C$_{14}$H$_{12}$O$_4$ (244.2): calculated: C 68.8%, H 5.0%, found: C 68.8%, H 5.1%.

EXAMPLE 6

4-Methyl-3-(2-methyl-3-oxobutyl)-maleic anhydride is prepared in a manner analogous to that described in Example 3, using 3-methyl-but-3-en-2-one in place of methyl vinyl ketone. This gives a pale yellow oil. $^1$H-NMR spectrum (100 MHz, CDCl$_3$, δ in ppm): 1.24 (d, J=7 Hz, 3H); 2.12 (s,3H); 2.20 (s,3H); 2.40 (m,1H); 2.71-3.26 (m,2H). IR spectrum (liquid, cm$^{-1}$): inter alia 1,780, 1,720, 1,285, 1,180, 1,120, 730.

Elementary analysis for C$_{10}$H$_{12}$O$_4$ (196.2): calculated: C 61.2%, H 6.2%, O 32.6%, found: C 61.0%, H 6.3%, O 32.5%.

EXAMPLE 7

4-Methyl-3-(2-methyl-3-phenyl-3-oxopropyl)-maleic anhydride is prepared in a manner analogous to that described in Example 3, using phenyl isopropenyl ketone in place of methyl vinyl ketone. This gives colourless crystals which, when recrystallised from isopropyl ether, melt at 89°-90° C. $^1$H-NMR spectrum (250 MHz, CDCl$_3$, δ in ppm): 1.30 (d, J=7 Hz, 3H); 2.16 (s,3H); 2.6 (m,1H); 3.02 (m,1H); 4.02 (m,1H); 7.46-7.68 (m,3H); 7.96 (m,2H).

Elementary analysis for C$_{15}$H$_{14}$O$_4$ (258.3): calculated: C 69.8%, H 5.5%, O 24.8%, found: C 69.8%, H 5.6%, O 24.9%.

EXAMPLE 8

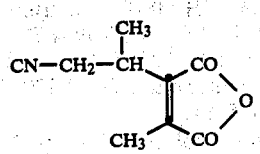

A solution of 4.4 g (0.11 mol) of sodium hydroxide in 30 ml of water and a solution of 8.7 g (0.13 mol) of crotononitrile in 70 ml of methanol are added in immediate succession to a mixture of 17 g (0.1 mol) of imidazo[1,2-a]pyridin-2(3H)-one hydrochloride and 40 ml of water. After stirring at room temperature for 36 hours, the mixture is evaporated to dryness at about 45° C. in vacuo, the residue is taken up in 120 ml of glacial acetic acid and, after the addition of 10.8 g (0.11 mol) of maleic anhydride and 4 g of sodium acetate, the mixture is boiled under reflux until the evolution of CO$_2$ has ended. The solvent is distilled off in vacuo, the crude product is taken up in a mixture of 60 ml of 6M sulfuric acid and 60 ml of tetrahydrofuran, and the resulting mixture is kept at 60° C. for 8 hours. After removal of the tetrahydrofuran in vacuo, the residue is diluted with water and extracted with methylene chloride. The organic phase is dried and evaporated and the residue is chromatographed on 500 g of silica gel with petroleum ether/methylene chloride. Distillation of the pure fractions in a bulb tube (140° C./10 Pa) gives 7.1 g (40% of theory) of 3-(2-cyano-1-methylethyl)-4-methyl-maleic anhydride as a pale yellow oil. (Crystallises after prolonged standing; melting point: 37°-39° C.). $^1$H-NMR spectrum (100 MHz, CDCl$_3$, δ in ppm): 1.48 (d, J=7 Hz, 3H); 2.21 (s,3H); 2.70-2.84 (m,2H); 3.28 (m,1H). IR spectrum (CH$_2$Cl$_2$, cm$^{-1}$): inter alia 1,790, 1,275, 1,150, 930, 905.

Elementary analysis for C$_9$H$_9$NO$_3$ (179.2): Calculated: C 60.3%, H 5.1%, N 7.8%; Found: C 60.5%, H 5.2%, N 7.8%.

EXAMPLE 9

4-Methyl-3-(1-methyl-3-oxobutyl)-maleic anhydride is prepared in a manner analogous to that described in Example 8, using pent-3-en-2-one in place of crotononitrile. This gives a pale yellow oil. $^1$H-NMR spectrum (100 MHz, CDCl$_3$, δ in ppm): 1.26 (d, J=7 Hz, 3H); 2.12 (s,6H); 2.60-3.50 (m,3H). IR spectrum (liquid, cm$^{-1}$): inter alia 1,780, 1,740, 1,370, 1,280, 1,180, 935, 910, 740.

Elementary analysis for C$_{10}$H$_{12}$O$_4$ (196.2): Calculated: C 61.2%, H 6.2%: Found: C 61.1%, H 6.2%.

EXAMPLE 10

4-Methyl-3-(3-oxocyclohexyl)-maleic anhydride is prepared in a manner analogous to that described in Example 8, using cyclohex-2-en-1-one in place of crotononitrile. Melting point: 106° C.–108° C. $^1$H-NMR spectrum (100 MHz, CDCl$_3$, δ in ppm): 1.60–2.57 (m,7H); 2.13 (s,3H); 2.71-3.27 (m,2H). IR spectrum (CHCl$_3$, cm$^{-1}$): inter alia 1,790, 1,730, 1,290, 1,270, 1,135, 940, 915, 735.

Elementary analysis for C$_{11}$H$_{12}$O$_4$ (208.2): Calculated: C 63.5%, H 5.8%: Found: C 63.5%, H 5.7%.

EXAMPLE 11

3-(1,3-Diphenyl-3-oxopropyl)-4-methyl-maleic anhydride is prepared in a manner analogous to that described in Example 8, using 1,3-diphenyl-propen-2-ene in place of crotononitrile. $^1$H-NMR spectrum (100 MHz, CDCl$_3$, δ in ppm): 2.19 (s,3H); 3.49–4.72 (ABX system, 3H); 7.23–7.60 (m,8H); 7.89–8.02 (m,2H). IR spectrum (CH$_2$Cl$_2$, cm$^{-1}$): inter alia 1,790, 1,720, 1,620, 1,510, 1,460, 1,220, 990, 935, 910.

Elementary analysis for C$_{20}$H$_{16}$O$_4$ (320.3): Calculated: C 75.0%, H 5.0%: Found: C 75.1%, H 5.1%.

EXAMPLE 12

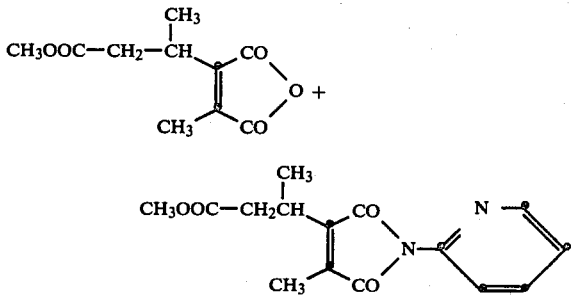

A solution of 4 g (0.1 mol) of sodium hydroxide in 30 ml of water and a solution of 14 g (0.14 mol) of methyl crotonate in 70 ml of methanol are added successively to a mixture of 17 g (0.1 mol) of imidazo[1,2-a]pyridin-2(3H)-one hydrochloride and 40 ml of water. After stirring at room temperature for 72 hours, the mixture is evaporated to dryness at about 45° C. in vacuo, the crude product is taken up in 150 ml of glacial acetic acid and, after the addition of 10.8 g (0.11 mol) of maleic anhydride and 5 g of sodium acetate, the mixture is boiled under reflux until the evolution of CO$_2$ has ended. The solvent is removed in vacuo and the residue is partitioned between water and methylene chloride. The crude product obtained after the organic phase has been dried and evaporated is chromatographed on 600 g of silica gel with petroleum ether/diethyl ether. This gives 6.4 g (30% of theory) of 3-(2-methoxycarbonyl-1-methylethyl)-4-methyl-maleic anhydride and 7.2 g (25% of theory) of 3-(2-methoxycarbonyl-1-methylethyl)-4-methyl-N-(pyrid-2-yl)-maleimide. Characterisation of the 3-(2-methoxycarbonyl-1-methylethyl)-4-methyl-maleic anhydride: $^1$H-NMR spectrum (100 MHz, CDCl$_3$, δ in ppm): 1.34 (d, J=7 Hz, 3H); 2.13 (s,3H); 2.50–3.04 (m, 2H); 3.32 (m,1H); 3.65 (s,3H). IR spectrum (CH$_2$Cl$_2$, cm$^{-1}$): inter alia 1,790, 1,760, 1,450, 1,280, 1,210, 1,185, 910.

Elementary analysis for C$_{10}$H$_{12}$O$_5$ (212.2): Calculated: C 56.6%, H 5.7%: Found: C 56.7%, H 5.7%.

Characterisation of the 3-(2-methoxycarbonyl-1-methylethyl)4-methyl-N-(pyrid-2-yl)-maleimide: $^1$H-NMR spectrum (100 MHz, CDCl$_3$, δ in ppm): 1.37 (d, J=7 Hz, 3H); 2.11 (s,3H); 2.53–3.08 (m,2H); 3.38 (m,1H); 3.65 (s,3H); 7.19–7.39 (m,2H); 7.81 (m,1H); 8.61 (m,1H). IR spectrum (CH$_2$Cl$_2$, cm$^{-1}$): inter alia 1,740, 1,610, 1,485, 1,450, 1,395, 1,185.

Elementary analysis for C$_{15}$H$_{16}$N$_2$O$_4$ (288.3): Calculated: C 62.5%, H 5.6%, N 9.7%: Found: C 62.4%, H 5.7%, N 9.9%.

EXAMPLE 13

12 g (0.3 mol) of sodium hydroxide in 150 ml of methanol and 150 ml of water, and 33.6 g (0.39 mol) of crotonic acid, are added successively, with stirring, to a mixture of 51.1 g (0.3 mol) of imidazo[1,2-a]pyridin-2(3H)one hydrochloride, 100 ml of water and 100 ml of methanol. After stirring at room temperature for 72 hours, the mixture is evaporated to dryness at about 45° C. in vacuo, the crude product is taken up in 500 ml of glacial acetic acid and, after the addition of 5 g of sodium acetate and 32.4 g (0.33 mol) of maleic anhydride, the mixture is boiled under reflux until the evolution of CO$_2$ has ended. The solvent is removed in vacuo, the crude product is taken up in a mixture of 200 ml of 6M sulfuric acid and 200 ml of tetrahydrofuran, and the resulting mixture is kept at 60° C. for 8 hours. After removal of tetrahydrofuran in vacuo, the residue is diluted with water and extracted with methylene chloride. The organic phase is dried and evaporated and the residue is filtered on silica gel with methylene chloride/diethyl ether. This gives 15 g (25% of theory) of 3-(2-carboxy-1-methylethyl)-4-methyl-maleic anhydride as a chromatographically pure solid with a melting point of 86° C.–88° C. Recrystallisation from diethyl ether/petroleum ether gives colourless crystals with a melting point of 90° C.–92° C. $^1$H-NMR spectrum (100 MHz, CDCl$_3$, δ in ppm): 1.37 (d, J=7 Hz, 3H); 2.12 (s,3H); 2.57–3.50 (m,3H); 10.9 (large s,COOH). IR-spectrum (KBr, cm$^{-1}$): inter alia 1,790, 1,735, 1,440, 1,415, 1,280, 1,240, 1,160, 960, 910, 740.

Elementary analysis for C$_9$H$_{10}$O$_5$ (198.2): Calculated: C 54.5%, H 5.1%: Found: C 54.5%, H 5.3%.

EXAMPLE 14

A mixture of 86 g (0.3 mol) of 3-(1,2-dicarboxyethyl)-imidazo[1,2-a]pyridin-2(3H)-one hydrochloride, 41.2 g (0.42 mol) of 3-ethyl-but-3-en-2-one, 110 ml of methanol and 110 ml of water is stirred for 36 hours at room temperature and then evaporated to dryness at about 45° C. in vacuo. The crude product obtained is taken up in 225 ml of glacial acetic acid, the solution is treated with 11 g of sodium acetate and the mixture is boiled under reflux until the evolution of $CO_2$ has ended. The solvent is then removed in vacuo, the residue is treated with a mixture of 110 ml of 6M sulfuric acid and 110 ml of tetrahydrofuran, and the resulting mixture is heated for 8 hours under reflux. After removal of tetrahydrofuran in vacuo, the reaction mixture is diluted with water and extracted with methylene chloride. The crude product remaining after the organic phase has been dried and evaporated is chromatographed on silica gel with methylene chloride. Subsequent distillation (110°–120° C./13 Pa) gives 3-(2-ethyl-3-oxobutyl)-4-methyl-maleic anhydride as a pale yellow oil.

EXAMPLE 15

A solution of 13.2 g (0.33 mol) of sodium hydroxide in 90 ml of water and a solution of 48.4 g (0.39 mol) of 1-acetylcyclohexene in 210 ml of methanol are added in immediate succession to a mixture of 51.2 g (0.3 mol) of imidazo[1,2-a]pyridin-2(3H)-one hydrochloride and 120 ml of water. After stirring at room temperature for 24 hours, the mixture is evaporated to dryness at about 45° C. in vacuo, the residue is taken up in 240 ml of glacial acetic acid and, after the addition of 29.4 g (0.3 mol) of maleic anhydride and 7.5 g of sodium acetate, the mixture is boiled under reflux until the evolution of $CO_2$ has ended. The solvent is distilled off in vacuo, the crude product is taken up in a mixture of 180 ml of 6M sulfuric acid and 180 ml of tetrahydrofuran, and the resulting mixture is heated for 8 hours under reflux. After removal of tetrahydrofuran in vacuo, the residue is diluted with water and extracted with methylene chloride. The organic phase is dried and evaporated and the residue is chromatographed on silica gel with petroleum ether/methylene chloride. Subsequent distillation (110°–115° C./13 Pa) gives 4-methyl-3-(1,2-tetramethylene-3-oxobutyl)-maleic anhydride as a pale yellow oil.

EXAMPLE 16

A mixture of 14.9 G (0.082 mol) of 4-methyl-3-(3-oxobutyl)-maleic anhydride and 5 g (0.082 mol) of ethanolamine is kept at 120° C. for 6 hours in an open flask. Subsequent distillation in a bulb tube (150° C./6 Pa) gives 9.4 g (50% of theory) of N-(2-hydroxyethyl)-4-metyl-3-(3-oxobutyl)-maleimide as a yellow oil. $^1$H-NMR spectrum (100 MHz, $CDCl_3$, δ in ppm): 1.95 (s,3H); 2.10 (s,3H); 2.45–2.85 (m,4H); 3.12 (large s, 1H, exchangeable with $D_2O$; 3.4–3.75 (m,4H). IR spectrum ($CH_2Cl_2$, cm$^{-1}$): inter alia 1,710, 1,400, 1,360, 1,165, 1,025.

Elementary analysis for $C_{11}H_{15}NO_4$ (225.2): Calculated: C 58.7%, H 6.7%, N 6.2%: Found: C 58.5%, H 6.9%, N 6.4%.

0.01598 mol of N-(2-hydroxyethyl)-4-methyl-3-(3-oxobutyl)-maleimide is introduced into a solution of 5 g of methyl vinyl ether/maleic anhydride copolymer in 86 ml of dry tetrahydrofuran and 0.1 ml of pyridine. The solution is stirred for 48 hours at 66° C. Diethyl ether is added to 20 ml of the solution and the precipitate formed is dried. From elementary analysis, it is calculated that 51.8% of the amount of N-(2-hydroxyethyl)-4-methyl-3-(3-oxobutyl)-maleimide used has been taken up.

Brushed aluminium plates are coated with the above solution. The plates are irradiated through a negative original (step wedge: Stouffer 21-Step Sensitivity Guide) with a 400 Watt metal halide lamp at a distance of 70 cm. The plate is then developed in tetrahydrofuran and sodium bicarbonate solution until the negative image appears.

Last step of which an image is formed after exposure for 1 minute: Step 1

Last step of which an image is formed after exposure for 3 minutes: Step 2

Last step of which an image is formed after exposure for 6 minutes: Step 4.

EXAMPLE 17

A mixture of 18.2 g (0.1 mol) of 4-methyl-3-(3-oxobutyl)-maleic anhydride and 22 g (0.105 mol) of morpholinium benzoate in 400 ml of benzene is heated under reflux for 48 hours, using a water separator. The benzene is removed in vacuo, the residue is taken up in methylene chloride and the organic phase is extracted twice with saturated sodium bicarbonate solution. The crude product remaining after the methylene chloride has been dried and removed in chromatographed on silica gel with petroleum ether/diethyl ether. This gives pale yellow crystals, which are recrystallised from methylene chloride/diethyl ether. This gives 3-methyl-6-morpholino-benzofuran-2(3H)-one with a melting point of 118°–121° C.

EXAMPLE 18

A mixture of 15.3 g (0.065 mol) of 4-methyl-3-(1,2-tetramethylene-3-oxobutyl)-maleic anhydride and 13.5 g (0.07 mol) of pyrrolidinium benzoate in 400 ml of benzene is heated under reflux for 60 hours, using a water separator. The benzene is removed in vacuo and the residue is partitioned between methylene chloride and saturated sodium bicarbonate solution. The crude product remaining after the methylene chloride has been dried and removed is chromatographed on silica gel with petroleum ether/diethyl ether. Subsequent recrystallisation from diethyl ether/petroleum ether gives 3-methyl-6-pyrrolidin-1-yl-4,5-tetramethylenebenzofuran-2(3H)-one with a melting point of 99°–101° C.

EXAMPLE 19

A cold solution of chlorine in chloroform is added dropwise at 0°–5° C., with stirring, to a mixture of 14.7 g (0.063 mol) of 3-methyl-6-morpholino-benzofuran-2(3H)-one and 100 ml of chloroform, until no further educt is visible in the thin layer chromatogram. The reaction mixture is diluted with methylene chloride and washed successively with 10% sodium thiosulfate solution, dilute sodium bicarbonate solution and water. The crude product remaining after the organic phase has been dried and evaporated is chromatographed on silica gel with petroleum ether/diethyl ether. After recrystallisation of the pure fractions from diethyl ether/petroleum ether, 5-chloro-3-methyl-6-morpholino-benzofuran-2(3H)-one with a melting point of 103°–105° C. is obtained.

EXAMPLE 20

5.4 g (0.02 mol) of 5-chloro-3-methyl-6-morpholino-benzofuran-2(3H)-one are dissolved in 40 ml of 1N sodium hydroxide solution at 50° C. After cooling, the solution is washed with diethyl ether and the aqueous phase is then adjusted to pH 2.0 with 1N hydrochloric acid. The oil thus formed is taken up in diethyl ether.

After evaporation of the diethyl ether, 2-(5-chloro-2-hydroxy-4-morpholinophenyl)-propionic acid is obtained as colourless crystals with a melting point of 198° to 200° C.

EXAMPLE 21

Tablets containing 25 mg of active ingredient, for example 3-methyl-6-pyrrolidin-1-yl-4,5-tetramethylenebenzofuran-2(3H)-one or a salt thereof, for example the hydrochloride, can be prepared in the following manner:

| Constituents (for 1,000 tablets): | |
|---|---|
| Active ingredient | 25.0 g |
| Lactose | 100.7 g |
| Wheat starch | 7.5 g |
| Polyethylene glycol 6000 | 5.0 g |
| Talc | 5.0 g |
| Magnesium stearate | 1.8 g |
| Demineralised water | q.s. |

PREPARATION

All the solid ingredients are first passed through a sieve with a mesh width of 0.6 mm. The active ingredient, the lactose, the talc, the magnesium stearate and half of the starch are then mixed. The other half of the starch is suspended in 40 ml of water and this suspension is added to a boiling solution of the polyethylene glycol in 100 ml of water. The starch paste obtained is added to the bulk and the mixture is converted to granules, water being introduced if necessary. The granules are dried overnight at 35°, passed through a sieve with a mesh width of 1.2 mm and compressed to tablets with a diameter of about 6 mm, which are concave on both sides.

EXAMPLE 22

Chewing tablets containing 30 mg of active ingredient, for example 5-chloro-3-methyl-6-morpholino-benzofuran-2(3H)-one or a salt thereof, for example the hydrochloride, can be prepared, for example, in the following manner:

| Composition (for 1,000 tablets): | |
|---|---|
| Active ingredient | 30.0 g |
| Mannitol | 267.0 g |
| Lactose | 179.5 g |
| Talc | 20.0 g |
| Glycine | 12.5 g |
| Stearic acid | 10.0 g |
| Saccharin | 1.0 g |
| 5% gelatin solution | q.s. |

PREPARATION

All the solid ingredients are first passed through a sieve with a mesh width of 0.25 mm. The mannitol and the lactose are mixed, converted to granules with the introduction of the gelatin solution, passed through a sieve with a mesh width of 2 mm, dried at 50° and again passed through a sieve, this time with a mesh width of 1.7 mm. The active ingredient, the glycine and the saccharin are carefully mixed, the mannitol, the lactose granules, the stearic acid and the talc are added and the whole is thoroughly mixed and compressed to tablets with a diameter of about 10 mm, which are concave on both sides and have a breaking notch on the upper side.

EXAMPLE 23

Tablets containing 100 mg of active ingredient, for example 2-(5-chloro-2-hydroxy-4-morpholinophenyl)-propionic acid or a salt thereof, for example the hydrochloride, can be prepared in the following manner:

| Composition (for 1,000 tablets): | |
|---|---|
| Active ingredient | 100.0 g |
| Lactose | 248.5 g |
| Maize starch | 17.5 g |
| Polyethylene glycol 6000 | 5.0 g |
| Talc | 15.0 g |
| Magnesium stearate | 4.0 g |
| Demineralised water | q.s. |

PREPARATION

The solid ingredients are first passed through a sieve with a mesh width of 0.6 mm. The active ingredient, the lactose, the talc, the magnesium stearate and half of the starch are then intimately mixed. The other half of the starch is suspended in 65 ml of water and this suspension is added to a boiling solution of the polyethylene glycol in 260 ml of water. The paste obtained is added to the pulverulent substances and the whole is mixed and converted to granules, water being added if necessary. The granules are dried overnight at 35°, passed through a sieve with a mesh width of 1.2 mm and compressed to tablets with a diameter of about 10 mm, which are concave on both sides and have a breaking notch on the upper side.

What is claimed is:

1. A process for the preparation of a compound of the formula I

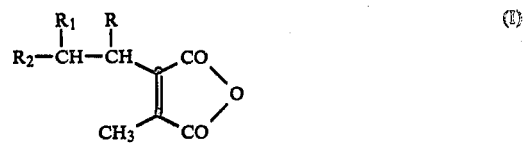

in which R is hydrogen, $C_{1-7}$-alkyl or phenyl which is unsubstituted or substituted by halogen, methoxy or $C_{1-4}$-alkyl, $R_1$ is hydrogen, $C_{1-7}$-alkyl, cyclopentyl, cyclohexyl or phenyl which is unsubstituted or substituted by halogen, methoxy or $C_{1-4}$-alkyl, or R and $R_1$ together are $-(CH_2)_3-$ or $-(CH_2)_4-$, and $R_2$ is $-CO-C_{1-8}$-alkyl, $-CN$, $-COO-C_{1-4}$-alkyl, $-COO-$allyl, $-COOH$ or $-CO-$phenyl which can be substituted by $C_{1-4}$-alkyl or in which $R_1$ is hydrogen and R and $R_2$ together are $-(CH_2)_3-CO-$, the carbonyl group in the ring formed in this way being in the m-position relative to the $-CH-$group which is attached to R, which comprises (a) in the case where R=H, firstly treating a compound of the formula II

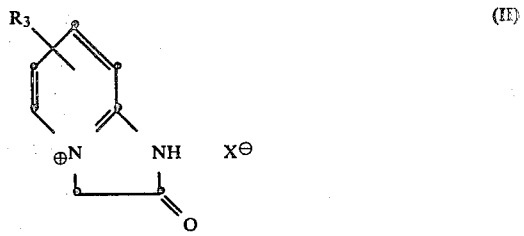

with fumaric acid, maleic acid or maleic anhydride, in the presence of a base, and then converting the product to a compound of the formula III

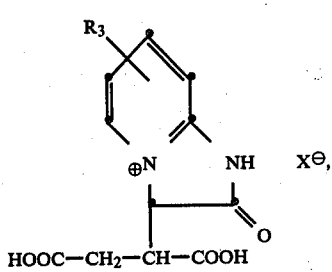  (III)

in the presence of a strong acid, reacting the compound of the formula III with a compound of the formula IVa $CH_2=C(R_1)(R_2)$  (IVa)

to give a compound of the formla V

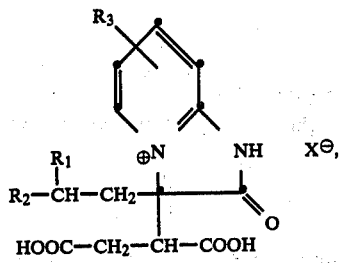  (V)

converting the compound of the formula V to a mixture of a compound of the formula I in which R=H and a compound of the formula VIa

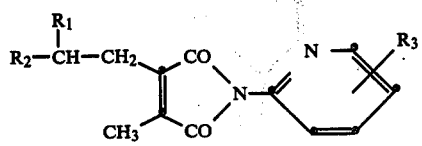  (VIa)

by heating to temperatures of between 80° and 160° C., and hydrolyzing the compound of the formula VIa with aqueous acid to give a compound of the formula I in which R=H, or (b) in the case where R is not H, firstly treating a compound of the formula II with a compound of the formula IVb $R'-CH=C(R_1)(R_2)$,  (IVb), in the presence of a base, and then reacting the product with fumaric acid, maleic acid or maleic anhydride, at temperatures of between 80° and 160° C., to give a mixture of a compound of the formula I in which R is not H and a compound of the formula VIb

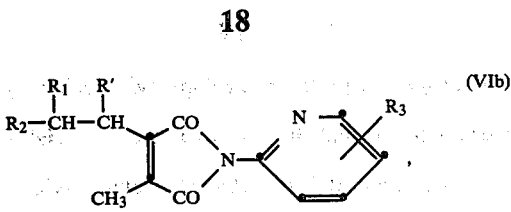  (VIb)

and hydrolyzing the compound of the formula VIb with aqueous acid to give a compound of the formula I in which R is not H, R, $R_1$ and $R_2$ being as defined in the formula I, R' having the same definition as R, but not being H, or, together with $R_2$, being $-(CH_2)_3-CO-$, in the case where $R_1=H$, the carbonyl group in the ring formed in this way being in the m-position relative to the $-CH-$ group, $R_3$ being hydrogen or methyl and $X^\ominus$ being the anion of an organic or inorganic acid.

2. A process according to claim 1, wherein maleic acid is used in process variant (a) and maleic anhydride is used in process variant (b).

3. A process according to claim 1, wherein an alkali metal hydroxide is used as the base.

4. A process according to claim 1, wherein the reaction of the compound of the formula II with fumaric acid, maleic acid or maleic anhydride is carried out in an aqueous medium and the reactions with the compounds of the formula IVa or IVb are carried out in an aqueous-alcoholic medium.

5. A process according to claim 1, wherein nitric acid, sulfuric acid or a hydrohalic acid is used as the strong acid.

6. A process according to claim 1, wherein the compounds of the formula V or the reaction mixture according to process variant (b) obtained after the addition of fumaric acid, maleic acid or maleic anhydride, are heated to temperatures of between 90° and 110° C., in the presence of glacial acetic acid.

7. A process according to claim 1, wherein the hydrolysis is carried out in an aqueous-inorganic acid mixed with a water-miscible organic solvent.

8. A compound of the formula I'

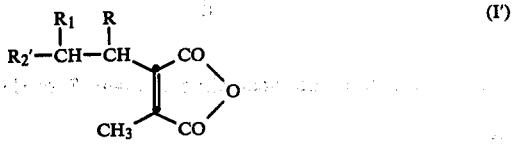  (I')

in which R is hydrogen, $C_{1-7}$-alkyl or phenyl which is unsubstituted or substituted by halogen, methoxy or $C_{1-4}$-alkyl, $R_1$ is hydrogen, $C_{1-7}$-alkyl, cyclopentyl, cyclohexyl or phenyl which is unsubstituted or substituted by halogen, methoxy or $C_{1-4}$-alkyl, or R and $R_1$ together are $-(CH_2)_3-$ or $-(CH_2)_4-$, and $R_2'$ is $-CO-C_{1-8}$-alkyl, $-CN$, $-COO-C_{1-4}$-alkyl, $-COO-$allyl, $-COOH$ or $-CO-$phenyl which can be substituted by $C_{1-4}$-alkyl but $R_2'$ is not $-COOH$ if R and $R_1$ are hydrogen, or in which $R_1$ is hydrogen and R and $R_2'$ together are $-(CH_2)_3-CO-$, the carbonyl group in the ring formed in this way being in the m-position relative to the $-CH-$ group which is attached to R.

9. A compound of the formula I', according to claim 8, in which $R_1$ is hydrogen and R and $R_2'$ together are $-(CH_2)_3-CO-$.

10. A compound of the formula I', according to claim 8, in which R is hydrogen, $C_{1-7}$-alkyl or phenyl and $R_1$ is hydrogen, $C_{1-7}$-alkyl, cyclopentyl, cyclohexyl or phenyl, or R and $R_1$ together are —$(CH_2)_3$— or —$(CH_2)_4$—, and $R_2'$ is —CO—$C_{1-8}$-alkyl, —CO—phenyl, —CN, —COOCH$_3$, —COOC$_2$H$_5$ or, if one of R and $R_1$ is not hydrogen, —COOH.

11. A compound of the formula I', according to claim 8, in which R and $R_1$ independently of one another are hydrogen or $C_{1-7}$-alkyl, or together are —$(CH_2)_3$— or —$(CH_2)_4$—, and $R_2'$ is —CO—$C_{1-8}$-alkyl.

12. A compound of the formula I', according to claim 8, in which one of R and $R_1$ is hydrogen and the other is hydrogen or $C_{1-4}$-alkyl, and $R_2'$ is —CO—$C_{1-5}$-alkyl.

13. A compound of the formula I', according to claim 8, in which R is hydrogen, $R_1$ is $C_{1-4}$-alkyl and $R_2'$ is —COCH$_3$.

14. The compound, according to claim 8, of the formula

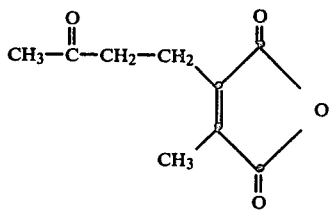

15. The compound, according to claim 8, of the formula

16. The compound, according to claim 8, of the formula

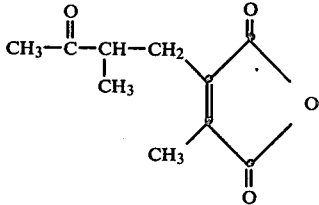

17. The compound, according to claim 8, of the formula

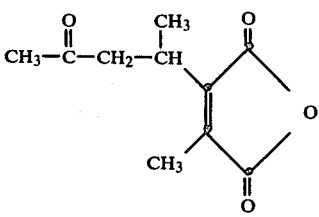

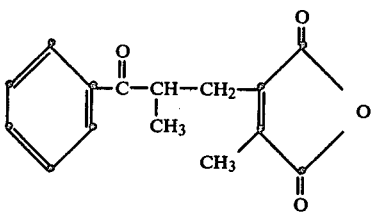

18. The compound, according to claim 8, of the formula

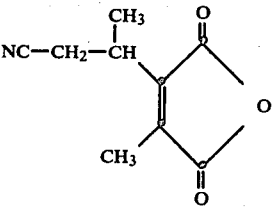

* * * * *